US 6,428,769 B1

(12) United States Patent
Rubsamen et al.

(10) Patent No.: US 6,428,769 B1
(45) Date of Patent: Aug. 6, 2002

(54) ACUTE TESTOSTERONE ADMINISTRATION

(75) Inventors: Reid M. Rubsamen, Alamo, CA (US); Robert Cole, 2519 Alamo County Cir., Alamo, CA (US) 94507

(73) Assignees: Aradigm Corporation; Robert Cole, both of Hayward, CA (US)

( * ) Notice: Subject to any disclaimer, the term of this patent is extended or adjusted under 35 U.S.C. 154(b) by 0 days.

(21) Appl. No.: 09/563,773

(22) Filed: May 2, 2000

Related U.S. Application Data

(60) Provisional application No. 60/132,472, filed on May 4, 1999.

(51) Int. Cl.[7] ............................. A61K 9/12; A61K 31/56
(52) U.S. Cl. ........................... 424/43; 424/46; 424/434; 514/253; 552/638
(58) Field of Search .................. 424/46, 238, 434, 424/43; 514/253; 552/638

(56) References Cited

U.S. PATENT DOCUMENTS

| 4,139,617 A | * | 2/1979 | Grunwell et al. | ............ 424/238 |
| 5,426,107 A | | 6/1995 | Bell et al. | ................ 514/234.2 |
| 5,536,714 A | | 7/1996 | Kojima et al. | ............... 514/169 |
| 5,874,064 A | * | 2/1999 | Edwards et al. | ............... 424/46 |
| 6,087,362 A | * | 7/2000 | El-Rashidy | ................. 514/253 |
| 6,200,591 B1 | * | 3/2001 | Hussain | ...................... 424/434 |

FOREIGN PATENT DOCUMENTS

WO    WO 97/29735    8/1997

OTHER PUBLICATIONS

Dialog® databse—File 351:Derwent WPI: "Non–occlusive, percutaneous, or transdermal drug delivery system—having active agent, safe and approved sunscreen as penetration enhancer, and optional volatile liquid."

* cited by examiner

Primary Examiner—Jose' G. Dees
(74) Attorney, Agent, or Firm—Karl Bozicevic; Bozicevic, Field & Francis LLP

(57) ABSTRACT

The libido of adult human female patients is increased by the intrapulmonary delivery of testosterone. A formulation of testosterone is aerosolized and inhaled into a patient's lungs where particles of testosterone deposits on lung tissue and then enter the patient's circulatory system. The patient's testosterone level is enhanced well above baseline levels for a short period and subsides to baseline levels with normal metabolism thereby providing desired short term effects on enhanced libido without undesirable effects of long term enhanced testosterone levels. Additional formulations are provided including formulations for aerosolized delivery of sildenafil citrate which are delivered to male or female patients.

16 Claims, No Drawings

ACUTE TESTOSTERONE ADMINISTRATION

CROSS-REFERENCES

This application claims priority to, and incorporates by reference in its entirety, earlier filed provisional patent application 60/132,472 filed May 4, 1999.

FIELD OF THE INVENTION

This invention relates generally to a method of treating women with a decreased libido. More specifically, the invention relates to acute non-invasive administration of testosterone to enhance libido over a discrete period of time.

BACKGROUND OF THE INVENTION

The presence of a normal amount of libido, defined as the urge to engage in sexual activity, is an important component of an individual's well-being. In both men and women the primary naturally occurring hormone responsible for libido is testosterone. In males, the baseline testosterone level is a relatively constant throughout life, decreasing slowly in old age. In contrast, women elaborate testosterone only as part of the process of ovulation. Each maturing follicle produces testosterone at the mid-point of the menstrual cycle, consistent with observations that female libido peaks with ovulation. As a woman ages, the number of maturing follicles per month decreases, and there is a decreasing total amount of testosterone produced.

A common complaint of post menopausal women is decreased libido. This decrease in libido is characterized by a lack of interest in sexual intercourse, the lack of ability to achieve orgasm, or decrease in intensity of orgasm. It is important to note that this decrease in libido is often associated with a profound sense of loss of a once normal and active interest in sexual activity.

Clinicians frequently confronted with the problem of managing female patients presenting with decreased libido have limited tools to address the problem. Testosterone is available as an oral preparation and can be given, for instance, in combination with estrogen to restore testosterone levels. However, the replacement of the once pulsatile endogenous delivery of testosterone with the sustained blood level of the hormone produces unwanted side effects. Women taking testosterone for a few weeks typically begin to complain of the emergence of secondary sexual characteristics such as unwanted body hair, oily hair, and, with prolonged a use, deepening voice. For this reason, oral testosterone replacement therapy is not a practical solution for most patients with decreased libido.

Other forms of testosterone replacement therapy for women are being explored. A transdermal patch capable of delivering a steady rate of testosterone is being tested for use in women. As with oral testosterone replacement therapy, the study state blood levels of testosterone produced via transdermal delivery are likely to be associated with the same side effect profile issues.

It is recognized that testosterone in females decreases with age (Human Biology, May 1980, volume of 52, No. 2, pages 181–0191.). It is also known that sexual motivation in post menopausal women is associated with the levels of exogenously introduced testosterone (Psychosomatic Medicine volume 47, No. 4, 1985). Further, providing intravenous testosterone to women as part of clinical studies is known (American Journal of Obstetrics and Gynecology, December 1986 pages 1288 to 1292).

SUMMARY OF THE INVENTION

A method of increasing the libido of a woman over a discrete period of time (e.g. 30–240 minutes) by the administration of testosterone is disclosed. A formulation comprised of testosterone is aerosolized preferably producing particles which have a size in a range of from about 1 to 3 microns which can be inhaled into areas of the lung where they can readily enter the blood stream. The aerosol is inhaled into the lungs of a patient. Once inhaled, particles of testosterone deposits on lung tissue and from there enter the patient's circulatory system and thereby increase the patient's serum testosterone level. The percentage increase in the patient's testosterone level will vary depending on the needs of the patient. However, the patient's normal baseline serum testosterone level is preferably increased 25% or more and more preferably 100% or more. Because delivery is by inhalation the patient's serum testosterone level is quickly raised to a desired level e.g. in thirty minutes or less, more preferably fifteen minutes or less. When the patient's testosterone level is raised to a desired level the patient's libido is increased. The increased testosterone level gradually subsides (as the testosterone is metabolized and cleared) thereby avoiding the adverse side effects generated by maintaining enhanced testosterone levels over long periods.

An aspect of the invention is a method of treatment whereby testosterone or derivative thereof is aerosolized, inhaled and provided to the circulatory system of the patient at levels sufficient to increase libido (over a short period of time) and propensity for orgasm.

An advantage of the invention is that the testosterone levels are raised within minutes of administration and return to normal levels within hours—preferably in less than four hours.

Another advantage is that the administered testosterone is quickly metabolized allowing the patient's testosterone levels to return to normal thereby avoiding the adverse effects of long term administration.

A feature of the invention is that aerosolized particles of testosterone having a diameter of about 0.5 to 8 microns (preferably 1–3 microns) are created and inhaled deeply into the lungs thereby enhancing the speed and efficiency of administration.

It is an object of this invention to describe the utility of delivering testosterone or dihydrotestosterone by inhalation as a means of treating women with decreased libido and/or decreased propensity to have orgasms.

It is another object of this invention to describe liquid formulations (which includes suspensions) of testosterone and derivatives thereof such as dihydrotestosterone appropriate for pulmonary delivery.

It is another object of this invention to describe how testosterone or dihydrotestosterone delivered via the lung can quickly increase plasma levels substantially beyond baseline levels for the patient.

It is another object of this invention to describe the blood levels of testosterone or dihydrotestosterone required for rapid onset of a normal to enhanced libido in women with baseline decreased libido.

It is another object of this invention to describe the time course of inhalation of testosterone or dihydrotestosterone and the onset of increased libido in women suffering from decreased libido.

It is another object of this invention to describe how the pulsatile delivery of testosterone or dihydrotestosterone as replacement therapy for women with decreased libido is associated with a decreased incidence of side effects (secondary sexual characteristics) commonly associated with traditional testosterone replacement therapy which produces a steady state level of the hormone.

The delivery of testosterone by inhalation provides, for the first time, the means for non-invasively delivering clinically relevant amounts of testosterone on demand near the time of planned intercourse.

It is an object of the invention to provide a method of treatment of erectile dysfunction in a patient comprising the steps of aerosolizing a formulation comprising sildenafil citrate, inhaling the aerosolized formulation into the lungs of a patient, and allowing the particles of sildenafil citrate to deposit on lung tissue and enter the patient's circulatory system.

It is an object of the invention to provide an aerosolized formulation comprised of sildenafil citrate and a carrier, the aerosol being characterized by particles having a diameter in the range of about 1.0 micron to 5.0 microns making up 50% or more of the aerosol particles.

It is an object of the invention to provide a kit comprising an aerosol delivery device and a formulation comprising a testosterone, sildenafil citrate, or a combination thereof.

It is an object of the invention to provide a kit comprising two aerosol delivery devices and two formulations, a first formulation comprising a testosterone for use by a women, and a second formulation comprising a testosterone, sildenafil citrate, or a combination thereof, for use by a man.

These and other aspects, objects, advantages, and features of the invention will become apparent to those skilled in the art upon reading this disclosure.

DEFINITIONS

The terms "testosterone", "a testosterone" and the like are used interchangeably here and are intended to mean the naturally occurring hormone known as testosterone having the chemical name 17-β-hydroxyandrost-4-en-3-one which may be isolated and purified from nature or synthetically produced in any manner. These terms are also intended to encompass the commonly occurring reduced version of testosterone having been reduced by 5α-reductase to 5α-dihydroxytestosterone which is also referred to here as dihydrotestosterone or simply "a testosterone." A dihydrotestosterone may be isolated from nature but is preferably synthetically produced and purified. Testosterone USP is a white or creamy-white crystalline powder having a molecular weight of 288.43.

The term "testosterone derivative" refers to any androgen hormone for pharmaceutical use. The term includes testosterone esters, i.e. compounds where the "H" of the "OH" group is replaced with an alkyl group, e.g. propionate, cypionate and enanthate. Other pharmaceutically acceptable derivatives include methyltestosterone, methandrostenolone, fluovymesterone and danazol. A number of useful derivatives of testosterone are disclosed within the Physician's Desk Reference (most recent edition) as well as Harrison's Principles of Internal Medicine. In addition, applicants refer to U.S. Pat. No. 5,536,714 issued Jul. 16, 1996; U.S, Pat. No. 5,824,668 issued Oct. 20, 1998; 3,980,638 issued Sep. 14, 1996; U.S. Pat. No. 4,031,117 issued Jun. 21, 1977; U.S. Pat. No. 4,085,202 issued Apr. 18, 1978; U.S. Pat. No. 4,197,286 issued Apr. 8, 1980; 4,507,290 issued Mar. 26, 1985 and U.S. Pat. No. 5,622,944 issued Apr. 22, 1997 all of which are incorporated herein by reference to disclose and describe testosterone derivatives and formulations.

The terms "diameter", "particle diameter" and the like are used interchangeably herein to refer to particle size as given in the "aerodynamic" size of the particle. The aerodynamic diameter is a measurement of a particle of unit density that has the same terminal sedimentation velocity in air under normal atmospheric conditions as the particle in question. This is pointed out in that it is difficult to accurately measure the diameter of small particles using current technology and the shape of such small particles may be continually changing. Thus, the diameter of one particle of material of a given density will be said to have the same diameter as another particle of the same material if the two particles have the same terminal sedimentation velocity in air under the same conditions. In connection with the present invention it is important to have particles which do not have too large of a diameter so that the particles can be inhaled deeply into the lungs and thereby deposited on lung tissue and transferred into the patient's circulatory system. It is equally important not to have particles which are too small in that such particles would be inhaled into the lungs and then exhaled without depositing on the lung tissue in the same manner that particles of smoke can be inhaled and exhaled with only a small amount of the particles being deposited on the lung tissue. An acceptable range for particle diameter is in the range of 0.5 to 12 microns, preferably 0.5 to 8 microns and more preferably 1 to 3 microns.

DESCRIPTION OF THE PREFERRED EMBODIMENTS

Before the devices, formulations, and methodology of the present invention are described, it is to be understood that this invention is not limited to the particular device, components, formulations and methodology described, as such may, of course, vary. It is also to be understood that the terminology used herein is with the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

All publications mentioned herein are incorporated herein by reference to described and disclose specific information for which the reference was cited in connection with. The publications discussed herein are provided solely for their stated disclosure prior to the filing date of the present application. Nothing herein is to be construed as an admission that the invention is not entitled to antedate such publications by virtue of prior invention. Further, the actual publication date may be different from that stated on the publication and as such may require independent verification of the actual publication dates.

INVENTION IN GENERAL

Despite the fact that steady state delivery of testosterone as replacement therapy for women experiencing decreased libido is inherently prone to producing unwanted side effects, the use of pulsatile testosterone replacement therapy to mimic the normal elaboration of this hormone during ovulation has not been explored. The use of testosterone replacement therapy for brief courses of treatment has been attempted, however the slow rate of absorption of methyl testosterone from pills has limited its utility. In order to replace the missing testosterone in a therapeutically effective manner, it is necessary to provide a rapid pulse of bioavailable testosterone to the patient on demand. In this way, testosterone could be replaced by the patient as needed coincident with the desire to engage in sexual activity.

It is not surprising that clinical studies evaluating the effect of acute, on demand testosterone replacement therapy in women with decreased libido have not been attempted. The only tool currently available for a true pulsatile, rapid onset replacement therapy is intravenous administration. Although preparations of testosterone appropriate for intravenous administrations have been available for some time, intravenous cannulation as the means for gaining access to the circulation for the administration of testosterone on demand is inconsistent with the desire for women to be able to modulate their libido in concert with the course of their daily lives.

Precision delivery of small molecule drugs via the lung for systemic effect is possible. An electronic inhaler capable of delivering a liquid formulated drug stored in a unit dose packages has been described. A formulation of testosterone or dihydrotestosterone can be prepared for delivery with this system. The quantitative delivery of testosterone or dihydrotestosterone, on demand by a woman prior to initiation of sexual intercourse, provides a mechanism for testosterone replacement therapy which is unlikely to be associated with side effects precipitated by chronic delivery of the drug.

While particularly applicable to post menopausal woman, the use of testosterone replacement therapy to modulate libido could be of value to women still of child bearing age. Disappearance of or reduction of the libido has been described in women who are continuing to ovulate. The reduction in libido may be due to therapy including the use of birth control pills which contain hormones. Therefore, acute administration of testosterone to significantly raise blood levels for discrete periods has potentially widespread application in women across a wide range of ages.

The baseline serum testosterone level of a normal adult human female is generally below about 1 ng/ml with modest changes through the menstrual cycle (Geobelmann et al., *Am J. Obstet. Gynecol.* 119:445 (1974)) with general fluctuation between about 0.3 to 0.5 ng/ml. However, adult human females with polycystic ovarian disease have ovarian vein testosterone levels of 20 to 65 ng/ml and peripheral venous levels of about 7.5 ng/ml (Dupon et al., *Am. J. Obstet. Gynecol.* 115:478 (1973)). Abnormally high levels of testosterone over long periods are associated with acne and hirsutism.

To maintain normal testosterone levels an adult human female will produce about 0.25 mg of testosterone per day as compared to about 5–6 mg/day produced by a normal adult mate to maintain a normal adult mate testosterone level of 3 to 10 ng/ml. Because women produce such small amounts of testosterone the administration of very small amounts will dramatically increase the patient's normal levels, In accordance with the present invention 0.05 mg to 5 mg, preferably 0.25 to 2 mg and more preferably about 1 mg of testosterone is administered to the circulatory system of the patient. Administration of such amounts to the circulatory system may require acrosolizing larger amounts due to inefficiencies in the aerosol delivery system In one embodiment the aerosolized formulation is delivered to an adult human female patient and the formulation comprises 0.25 mg or more of testosterone which increases the patient's testosterone level to 0.8 ng/ml or more in fifteen minutes or less.

Testosterone can be administered orally. However, after oral administration it is absorbed from the gut into the portal blood and degraded promptly by the liver. Thus, insignificant amounts reach the patient's systemic circulation. Testosterone can also be administered parenterally. However, when so administered it is rapidly absorbed and metabolized making it difficult to sustain effective levels in plasma over time. In view of such, effective therapy has been carried out using means of delivery where testosterone is slowly absorbed (e.g. dermal patches) or when the testosterone is chemically modified to retard absorption and/or catabolism.

The present invention uses intrapulmonary delivery to avoid first pass liver metabolism and to obtain quick infusion into the patient's systemic circulatory system. Further, the method of the present invention does not require maintaining increased testosterone levels over long periods. Accordingly, chemical modification to retard absorption and/or catabolism are not required or desired.

The present invention administers sufficient testosterone by inhalation to temporarily raise the patient's libido, increase the patient's propensity for orgasm, and thereafter allow the patient's testosterone level to return to a level normally experienced by the patient. Because intrapulmonary administration is not 100% efficient the amount of drug aerosolized will be greater than the amount which actually reaches the patient's circulation. For example, if the inhalation system used is only 50% efficient then the patient will aerosolize a dose which is twice that needed to raise the patient's testosterone level to the extent needed to obtain the desired results. More specifically, when attempting to administer 1 mg of testosterone with a delivery system known to be 50% efficient the patient will aerosolize an amount of formulation containing about 2 mg of testosterone.

Testosterone therapy as described herein can be used in construction with other therapies intended to increase or enhance libido. Such therapies include but are not limited to herbal preparations and vitamin supplements.

INDICATIONS

The method of the invention has broad applicability to both the male and female populations. However, its use is specifically indicated in four categories.

First, post-menopausal women who have experienced all or any of (1) decreased levels of testosterone; (2) decreased libido; and (3) decreased propensity to experience orgasm.

Second, women of child bearing age who have experienced all or any of (1) decreased levels of testosterone; (2) decreased libido; and (3) decreased propensity to experience orgasm.

Thirdly, women of child bearing age being treated with birth control pills who have experienced all or any of (1) increased levels of estrogen relative to testosterone resulting in either or both of (2) decreased libido and (3) decreased propensity to experience orgasm.

Fourthly, men having erectile dysfunction symptoms, especially those due to peripheral vascular disease.

Fifthly, men having a decreased level of serum testosterone.

In the first three categories it is not desirable to administer sufficient amounts of a testosterone so as to raise the patient's testosterone level continually over long periods of time. For example, it is not desirable to administer testosterone several times per day for several days. Such will raise testosterone levels over long periods and result in adverse side effects including acne, and increased growth of body hair.

DOSING

The amount of a testosterone administered will vary based on a factor such as the age, weight and baseline testosterone level of the patient. Initially, small doses, e.g. about 0.25 mg, is administered. If the desired result is obtained no further dosing is provided. If desired effect is not obtained additional 0.25 mg doses can be administered up to 2.0 mg. If the patient finds that larger doses are needed then for further treatment the patient may be provided with doses of 0.5 mg, 1.0 mg or 2.0 mg. The amount aerosolized may be substantially greater than the amount administered if the interpulmonary delivery device is inefficient. Thus, the device and method efficiencies must be taken into consideration when calculating the doses.

When testosterone enters the circulatory system of a human patient it is readily reduced via 5α-reductase to 5α-dihydrotestosterone. Thus, when referring to increasing a patient's testosterone level this disclosure is referring to combined levels of testosterone and 5α-dihydroxytestosterone present in the patient's serum. The present invention includes the administration of 5α-dihydroxytestosterone which is the active molecule. The invention also includes the administration of testosterone derivatives provided such derivatives increase libido and do not result in unacceptable adverse effects.

Obtaining a result such as increased libido may be difficult to ascertain. Some placebo effect will be experienced by some patients and others may continuously administer doses in an attempt to obtain a more enhanced effect. To avoid undesirable side effects from overdosing or from dosing to frequently the delivery device may be controlled by a suitable lockout system such as taught in U.S. Pat. Nos. 5,507,277; 5,694,919; and 5,735,263. Such a system can prevent release of more than a given amount of drug at a single dosing event and/or restrict the number of dosing events within a given period of time. The restrictions are designed to prevent the patient from experiencing adverse secondary effects.

FORMULATIONS/DEVICES

Pharmaceutical grade testosterone can be produced as a white or creamy white powder. The pure powder is aerosolized and inhaled by itself or with the use of a dry powder inhaler (DPI) device. However, it is desirable to formulate the crystals with an excipient to provide small particles of dry powder which do not stick together. The particles preferably have a diameter in a range of from about 1 to 10 microns more preferably 1 to 5 microns and still more preferably about 1 to about 3 microns. Methods of formulating dry powders and dry powder inhaler devices are disclosed in U.S. Pat. Nos. 5,814,607; 5,785,049; 5,780,014; 5,775,320; 5,740,794; and Des. 390,651 all of which are incorporated by reference to describe and disclose such.

Testosterone is relatively insoluble in water. Accordingly, to create a solution of testosterone a solubilizer (e.g., one of several cyclodextrines or phospholipids) or an organic solvent such as ethanol is used. Alternatively, a microsuspension of testosterone in water with or without ethanol can also be produced. The testosterone solution is aerosolized and inhaled. The testosterone solution can be placed in a low boiling point propellant in a pressurized canister and released using a conventional metered dose inhaler (MDI) device. Preferably, the MDI device is modified so that the aerosolized dose is released each time at the same inspiratory flow rate and inspiratory volume. When this is done the patient is more likely to receive the same dose each time. A device for obtaining repeatable dosing with an MDI canister is taught in U.S. Pat. No. 5,404,871 issued Apr. 11, 1995.

In accordance with the present invention it is preferable to load the testosterone solution into a container which opens to a porous membrane. When the formulation is moved through the membrane it is aerosolized. Such containers are taught in U.S. Patent 5,497,763 issued Mar. 12, 1996. The container is loaded into a device and delivered via a method as taught in U.S. Pat. No. 5,823,178 issued Oct. 10, 1998 both of which patents are incorporated herein by reference to describe and disclose containers, devices and methods of drug delivery by inhalation.

Aerosol drug delivery devices vary but generally are comprised of (1) a container for the drug e.g. testosterone; (2) a means for aerosolizing the drug; and (3) a mouthpiece from which the aerosol is inhaled. The aerosol can be any small particles dispersed in air, e.g. a cloud of a dry powder or a fine spray of liquid formulation. Nebulizers, metered dose inhalers (MDIs) and dry powder inhalers (DPIs) are the most well known devices for creating an aerosol. Less conventional devices known as electrohydrodynamic aerosol devices as taught in U.S. Pat. No. 4,358,059; PCT WO 99/07478; and 98/03267 can also be used to create an aerosol in the method of the invention.

Nasal or buccal formulations could be used for nasal or buccal delivery.

AEROSOL ADMINISTRATION OF SILDENAFIL

Similarly, agents such as sildenafil citrate (U.S. Pat. No. 5,426,107 and U.S. Pat. No. 5,250,534) can also be administered to women or men by the methods of the instant invention, alone or in combination with testosterone.

Sildenafil citrate, also termed VIAGRA™, is typically administered in tablet form to men experiencing erectile dysfunctions resulting from peripheral vascular disease. The tablet is taken orally about thirty (30) minutes to four (4) hours before sexual activity.

The typical oral dose of sildenafil is 25–100 mg per day. As described above, such doses can be administered to the lungs through the use of aerosolized aqueous solutions or as a dry powder.

The sildenafil citrate can be formulated alone or as an admixture with a testosterone for simultaneous delivery.

In an embodiment, men in need of supplemental testosterone and experiencing erectile dysfunction due to peripheral vascular diseases can administer the drugs either simultaneously or sequentially. The dosage of testosterone will typically be sufficient to raise the serum testosterone level of the man to a normal range, that being about 200–1000 ng/dL.

The formulation of sildenafil citrate can be administered to male or female patients and may be administered alone or in combination with an aerosolized dose of testosterone.

In one embodiment of the invention the sildenafil citrate is administered orally and the testosterone is administered by aerosol about 30–60 minutes after the oral administration of sildenafil citrate. The oral administration of sildenafil citrate is an administration in advance of a sexual event and after allowing time to achieve a therapeutic effect on increasing blood flow the patient is dosed with testosterone via aerosol. The testosterone enhances the libido and the sildenafil citrate enhances the patient's ability to perform and/or achieve orgasm.

The aerosolized administration of testosterone could also be in combination with other drugs used in the treatment of various sexual dysfunctions e.g. administered in combination with the topical application of alprostadil. Other oral, injectable and topical drugs are and will become available for the treatment of sexual dysfunctions and such drugs (e.g. vasodilators) can be used in combination with aerosolized delivery of testosterone to obtain enhanced results. It is noted that although such drugs may, by themselves, facilitate sexual activity they do not effect libido. Accordingly, a truly enhanced effect is obtainable by combining a drug which increases blood flow to a desired area with aerosolized delivery of testosterone which increases libido.

KITS

In an embodiment of the invention, a kit is provided for use by a healthcare provider, more preferably a patient. An exemplary kit will provide a hand-held aerosol delivery device and at least one dose, preferably one to about one hundred, more preferably one to thirty doses of a testosterone for use by a women. In an embodiment, the kit will comprise a hand-held aerosol delivery device and at least one dose, preferably one to about one hundred, more preferably one to thirty doses of a testosterone for use by a man. In an embodiment, the kit will provide a hand-held aerosol delivery device and at least on dose, preferably one to about one hundred, more preferably one to thirty doses of an admixture of testosterone and sildenafil citrate for use by a man. In an embodiment, the kit will contain a hand-held aerosol delivery device and at least one dose, preferably one to about one hundred, more preferably about one to thirty doses of sildenafil citrate for use by a man.

In an embodiment, a kit is provide with comprises two hand-held delivery devices, wherein a first delivery device comprises at least one dose, preferably one to one hundred doses, of a testosterone for use by a woman. The second delivery device comprises at least one dose, preferably one to one hundred doses, of a testosterone, sildenafil citrate, or a combination thereof for use by a man. Such a kit is intended for use by a couple in need of such treatment.

The kit of the invention can be comprised of various combinations of drugs and drug delivery devices. However, the kit will preferably be comprised of an aerosol drug delivery device which comprises a container which holds one or a plurality of doses of testosterone, a means for aerosolizing the testosterone and a mouthpiece from which the aerosolized testosterone may be inhaled. This device is present in the kit with another drug. For example, the kit may comprise a container of sildenafil citrate or related drug which obtains a response similar to sildenafil citrate. The other drug may be administered orally or topically but is preferably in a container which can be loaded into the device used to deliver the testosterone by inhalation. Thus, a preferred kit will comprise a drug delivery device which can generate an aerosol for inhalation and a plurality of containers of testosterone which can be loaded into the device and a plurality of containers of a vasodilator such as sildenafil citrate which can be loaded into the device.

The instant invention is shown and described herein in a manner which is considered to be the most practical and preferred embodiments. It is recognized, however, that departures may be made therefrom which are within the scope of the invention and that obvious modifications will occur to one skilled in the art upon reading this disclosure.

What is claimed is:

1. A method of increasing serum testosterone, comprising the steps of:
   aerosolizing a formulation comprising a testosterone;
   inhaling the aerosolized formulation into lungs of a patient; and
   allowing particles of the testosterone to deposit on lung tissue, enter the patient's circulatory system and thereby increase the patient's serum testosterone level, wherein the patient's serum testosterone level is increased above the patient's normal baseline testosterone serum level by 25% or more in thirty minutes or less.

2. The method of claim 1, wherein the patient's testosterone level is increased above the patient's normal baseline serum level by 100% or more.

3. The method of claim 1, wherein the patient's testosterone level is increased from a first level to a second increased level which is twice or more the first level.

4. The method of claim 3, wherein the patient's serum testosterone level is increased in fifteen minutes or less and wherein the aerosolized formulation comprises 0.25 mg or more of testosterone and further wherein the patient's testosterone level is increased to 0.8 ng/ml or more.

5. The method of claim 1, wherein the patient is an adult human female, the testosterone is dihydrotestosterone, and the patient's dihydrotestosterone level is increased to about 0.8 ng/ml or more in fifteen minutes or less.

6. The method of claim 1, wherein the patient is an adult human male.

7. The method of claim 1, further comprising:
   aerosolizing a formulation of sildenafil citrate;
   inhaling the aerosolized formulation into the lungs of the patient; and
   allowing particles of the sildenafil citrate to deposit on lung tissue and enter the patient's circulatory system.

8. A method of increasing libido, comprising the steps of:
   aerosolizing a therapeutically effective amount of a formulation comprising a testosterone;
   inhaling aerosolized particles of the testosterone into the lung of a patient;
   allowing the particles to deposit on lung tissue and enter the patient's circulatory system in an amount sufficient to increase the patient's libido above the patient's libido level prior to inhaling the particles of testosterone and the patient's testosterone serum level is increased above the patient's normal baseline testosterone serum level by 25% or more in thirty minutes or less.

9. The method of claim 8, wherein the testosterone is dihydrotestosterone and the patient is an adult human female and the patient's testosterone serum level is increased above the patient's normal baseline testosterone serum level by 100% or more in fifteen minutes or less.

10. The method of claim 8, wherein the aerosolized particles are comprised of particles having a diameter in a range of from about 1 to about 5 microns.

11. The method of claim 8, wherein the formulation is a dry powder formulation comprising a testosterone and a carrier.

12. The method of claim 8, wherein the formulation is a liquid formulation comprising a testosterone and an excipient selected from the group consisting of an organic solvent to form solutions and a liquid to form suspensions.

13. A method of increasing a patient's propensity to experience orgasm, comprising the steps of:
   aerosolizing a formulation comprising a testosterone to create particles having a diameter in a range of from about 1 to about 10 microns;
   inhaling the particles into lungs of a patient; and
   allowing particles of the testosterone to deposit on lung tissue, enter the patient's circulatory system and thereby increase the patient's serum testosterone level in an amount sufficient to increase the patient's propensity to experience orgasm.

14. The method of claim 13, wherein the formulation comprises a dry powder of a testosterone and a carrier and 50% or more of the particle having a diameter in a range of from about 1 to about 3 microns.

15. The method of claim 13, wherein the formulation comprises a solution or suspension of a testosterone and an organic solvent or liquid carrier and the aerosolized particles are created by moving the formulation through a porous member.

16. The method of claim 14, wherein the organic solvent is ethanol and 50% or more of the particles have a diameter in a range of from about 1 to about 3 microns.

* * * * *